United States Patent [19]

Carter et al.

[11] Patent Number: 5,124,349
[45] Date of Patent: * Jun. 23, 1992

[54] STORAGE STABLE AZADIRACHTIN FORMULATION

[75] Inventors: Charles G. Carter, Silver Spring; Clifford J. Hull, Jr., Laurel; Narender P. Luthra, Columbia; James F. Walter, Ashton, all of Md.

[73] Assignee: W. R. Grace & Co.-Conn., New York, N.Y.

[*] Notice: The portion of the term of this patent subsequent to Mar. 19, 2008 has been disclaimed.

[21] Appl. No.: 606,366

[22] Filed: Oct. 31, 1990

Related U.S. Application Data

[63] Continuation-in-part of Ser. No. 371,243, Jun. 26, 1989, Pat. No. 5,001,146.

[51] Int. Cl.$^5$ ............................................. A01N 43/16
[52] U.S. Cl. .................................... 514/453; 424/195.1
[58] Field of Search ...................... 424/195.1; 514/453

[56] References Cited

U.S. PATENT DOCUMENTS 4,556,562 12/1985 Larson .............................. 424/195.1

OTHER PUBLICATIONS

J. of Liquid Chromatography, 2(6), 875-882 (1979), Uebel et al.
Fd. Chem. Toxic. vol. 25, No. 10, 763-766 (1987) Polasa et al.
Neem Newsletter 5(4) p. 48 (1988) Muthusamy et al.
J. Econ. Entomol. 77, 903-905 (1984) Ladd et al.
J. Environ. Sci. Health, A17(1), 57-65 (1982) Stokes et al.
J. of Plant Diseases and Protection, 89(12), 737-747 (1982) Feuerhake et al.
J. of Natural Products, vol. 50, No. 2, 241-244 (1987) Schroeder et al.
J. of Liquid Chromatography, 7(3) 591-598 (1984), Warthen et al.
Science and Education Administration, Agricultural Reviews and Manuals, Northeastern Series, No. 4, (1979), Warthen, Jr.
Schmutterer, "Potential of Azadirachtin-Containing Pesticides for Integrated Pest Control in Developing and Industrialized Countries," *J. Insect Physiol.*, vol. 34, No. 7, pp. 713-719 (1988).

*Primary Examiner*—Johnnie R. Brown
*Assistant Examiner*—A. Varma
*Attorney, Agent, or Firm*—Jill H. Krafte

[57] ABSTRACT

Storage stable pesticide compositions comprising neem seed extracts which contain azadirachtin as the active pesticidal ingredient wherein the compositions are characterized by their non-degrading solvent systems. In a first embodiment, the pesticide compositions contain solvent systems characterized as having greater than 50% by volume aprotic solvents and less than 15% by volume water. In a second embodiment, the pesticide compositions contain solvent systems characterized as having greater than 50% by volume alcohol and less than 5% by volume water. The pesticide compositions contain surfactant concentrations of at least about 1.0%, up to 10%.

19 Claims, No Drawings

STORAGE STABLE AZADIRACHTIN FORMULATION

This is a continuation-in-part of copending U.S Ser. No. 371,243, filed Jun. 26, 1989 (Carter, Hull, Luthra and Walter), now U.S. Pat. No. 5,001,146.

BACKGROUND OF THE INVENTION

1. Field of the Invention

This invention relates to pesticide compositions, and more specifically to storage-stable pesticide formulations containing azadirachtin as the active ingredient.

2. Description of the Prior Art

The biological activities of the neem tree seeds have long been recognized. Of primary importance are the potent pesticidal properties of azadirachtin, the main active ingredient in the neem seed. Azadirachtin is a tetranortriterpenoid that causes feeding inhibition and growth disruption in various insect, mite, nematode, etc. orders.

There are various methods known in the prior art to extract azadirachtin from neem seeds, including the use of solvents such as methanol, ethanol, water, methylene chloride, chloroform, hexane, methylethylketone, butanol, petroleum benzene, ether, acetone, methyl tertbutyl ether, diethylcarbonate, etc. In general, it has been found that the efficiency of the extract yield can be increased by increasing the solvent polarity, i.e., from hexane to ethanol, ethanol to methanol, methanol to water, etc. However, while various studies have examined relative solvent extraction efficiencies, little attention has focused on the shelf life stability of azadirachtin in solution.

The most significant limitation to the successful use of azadirachtin as a pesticide and insect repellant is the ability of the azadirachtin in solution. One study has shown that heat and sunlight (UV radiation) cause rapid degradation of azadirachtin. *J. Environ. Sci. Health,* A17(1), 57–65 (1982) by J. B. Stokes and R. E. Redfern. Sunlight degradation of azadirachtin can be effectively reduced by addition of UV absorbing additives such as para-aminobenzoic acid (PABA), neem oil, angelica oil, castor oil, or calmus oil.

Other factors known to affect the storage stability of azadirachtin are the concentration of azadirachtin in solution and the pH of the solution. U.S. Pat. No. 4,556,562 (Larson) discloses improvement in storage properties of azadirachtin in aqueous ethanol emulsions by adjusting the concentration of azadirachtin in the range 2000 to 4000 ppm and adjusting the pH in the range 3.5 to 6.0.

It now has been discovered that the stability of azadirachtin in solution is decreased in the presence of protic solvents, in particular water, acids and bases.

SUMMARY OF THE INVENTION

It is an object of this invention to provide a non-toxic, natural pesticide formulation based on an extract from neem seeds with improved storage stability.

Another object of this invention is to provide a process for preparing storage stable azadirachtin formulations wherein the formulation is characterized by its non-degrading solvent system.

Another object of this invention is to provide a storage stable neem seed extract formulation having azadirachtin as the active pesticidal ingredient wherein the formulation is characterized by incorporating solvents which are non-degrading toward azadirachtin.

In accordance with the present invention, there have been provided certain novel pesticide formulations containing azadirachtin as an active ingredient, said formulations characterized by the particular non-degrading nature of the solvent system with respect to azadirachtin. As used herein, the term non-degrading relates to aprotic solvents that do not cause the decomposition of azadirachtin in solution. The aprotic solvents of this invention are characterized by the absence of any acidic or basic functionalities. The azadirachtin formulations of this invention, by virtue of their non-degrading solvent systems, offer improved shelf life stability over the prior art ethanol-water based formulations.

DETAILED DESCRIPTION

The present invention is directed to storage stable azadirachtin compositions which have been formulated using non-degrading solvent systems. As used herein, the term "storage stable" refers to formulations that have retained at least 80% of their active ingredient content after one year at room temperature (25° C.). It has now been discovered that the stability of azadirachtin is substantially decreased by the presence of protic solvents, in particular those solvents having acidic or basic functional groups specifically water, acids and bases. There are basically two non-degrading solvent systems acceptable for use in the azadirachtin formulations of the invention, namely alcohols and "aprotic" solvents. In accordance with the present invention, azadirachtin formulations with enhanced stability are obtained when the solvent system of the formulation is comprised of either greater than 50% by volume alcoholic solvents containing less than 5% water, or greater than 50% by volume aprotic solvents containing less than 15% water. The compositions covered in this application contain one or more surfactants in total concentration of at least about 1.0%, up to 10%.

Aprotic solvents are defined as polar solvents having moderately high dielectric constants, which do not contain acidic hydrogen, Morrison and Boyd, *Organic Chemistry* 3rd. Edition, 31 (1974). The various factors that determine whether a given solvent is protic or aprotic are only qualitatively understood. The proton donating or proton accepting interaction is usually greatest when the atom attached to the proton is nitrogen or oxygen. This behavior has been attributed to hydrogen bonding. In general, the hydrogen bond strength increases with increasing acidity of the proton-donating group, and increasing basicity of the proton-accepting group. Aprotic solvents suitable for use in this invention will be those solvents that do not contain acidic or basic functional groups and do not degrade into acids or bases, including, but not limited to, ketones, nitriles, substituted aromatics such as alkyl or halogenated aromatics, amides, sulfoxides, alkyl carbonates, chlorinated aliphatics, aromatic aldehydes, sulfones, ethers, esters, and the like, or mixtures thereof. The preferred aprotic solvents for use in this invention include, but are not limited to, acetone, 2-butanone, 3-methyl-2-butanone, cyclohexanone, acetonitrile, xylenes, chlorobenzene, methylene chloride, chloroform trichloroethane, ethylene chloride benzaldehyde, sulfolane, methyl-t-butyl ether, dibutyl ether, ethyl acetate, propyl acetate, amyl acetate, dimethylsulfoxide (DMSO), dimethylformamide (DMF), dimethylacetamide, diethylcarbonate, propylene carbonate, ethylene carbonate, and mixtures thereof. Various other solvents having the above aprotic characteristics are known to those skilled in the art, and the choice of a particular solvent is not per se critical to the invention, provided that azadirachtin has a high degree of solubility therein, and the solvent does not cause degradation of the azadirachtin by proton donating or proton accepting interactions.

Suitable alcoholic solvents for use in this invention include, but are not limited to, methanol, ethanol, propanol, isopropanol, butanol, 2-butanol, t-butanol, benzyl alcohol, and the like, and mixtures thereof.

Solvents which are unacceptable for use in the solvent systems of this invention are those protic solvents characterized by the presence of acidic or basic functional groups which can undergo proton-transfer reactions that result in charged species such as $RCOO^-$ or $RNH_3^+$. Those solvents known to degrade azadirachtin include bases such as amines or hydroxides, acids such as mineral acids or carboxylic acids. However, the final azadirachtin formulations of this invention may contain minor amounts of these solvents, typically less than 1% by volume for the control of pH and the like.

The storage stable azadirachtin formulations of this invention can be prepared by either of two general procedures.

A first embodiment of this invention is to extract azadirachtin and neem oil together from dried neem seeds that have been coarsely ground to about 5 mesh. The ground neem seeds are extracted by using a polar solvent having azadirachtin solubility. If desired, the polar solvent extraction may be repeated to optimize the extraction efficiency.

Because dried neem seeds retain between 6 and 15% water, this polar solvent extraction, in addition to extracting azadirachtin, also extracts a significant amount of water. The neem seed extracts typically contain about 20% by volume water. Since water is an azadirachtin-degrading, protic solvent, its presence in neem seed extracts above the previously defined allowable limits will reduce the storage stability of the azadirachtin formulations. It has been discovered that the allowable limit to the amount of water in a neem seed extract is dependent upon the aprotic/protic character of the particular solvent system of the extract. Specifically, if the solvent system is comprised of greater than 50% by volume aprotic solvents such as ketones or esters, the concentration of water must be less than 15% by volume of the total solution. Alternatively, if the solvent system comprises greater than 50% alcohol solvents, (which are more protic) the concentration of water must be less than 5%, preferably less than 2%, and most preferably less than 1% by volume of the total solution.

There are various techniques to reduce the concentration of water in the final solutions to within the above defined acceptable limits including, but not limited to, further extracting the neem seed extracts with a water-immiscible solvent, diluting the extracts with an appropriate aprotic solvent, or drying the extracts over a suitable adsorbent.

A preferred embodiment of this invention is to extract dried neem seeds that have been milled to a coarse powder of about 5 mesh with a non-polar, azadirachtin-insoluble aprotic solvent such as hexane to remove the neem oil from the seeds. This "cleanup" extraction is then followed by a second extraction of the defatted neem seeds using a more polar, azadirachtin-soluble solvent. As in the first embodiment, this extraction may be repeated to optimize the extraction efficiency.

The final azadirachtin pesticide formulations of this invention preferably contain at least about 1.0 up to 10% emulsifying surfactant, 0 to 40% neem oil, 0 to 1% para-aminobenzoic acid or its esters, and less than 1% acetic acid or sodium hydroxide to adjust the pH to between about 3.8 and 4.2.

Without further elaboration, it is believed that one skilled in the art, using the preceding detailed description can utilize the present invention to its fullest extent.

The following examples are provided to illustrate the invention in accordance with the principles of this invention, but are not to be construed as limiting the invention in any way except as indicated in the appended claims. All parts and percentages are by weight unless otherwise indicated.

EXAMPLE 1

Two kgs of neem seeds were first milled to a coarse powder of approximately 5 mesh and then extracted with hexane under mild agitation for 24 hours to remove the neem oil. A 0.5 kg portion of the oilless seeds was then extracted with 1 liter of 95% ethanol at 70° C. for four hours to remove the azadirachtin. The ethanol extraction was repeated twice more on the remaining portions of ground neem seeds, yielding a final extract having a composition of 4.5 g/l azadirachtin and 16.5% $H_2O$. The ethanolic extract was separated into 4–100 mls samples. To these, 3A° mole sieves were added at the rate of 20, 30, 40, 80 g of sieves per sample. The samples were sealed and analyzed after agitating 12 hours at room temperature. The results are presented in Table I.

TABLE I

| Sample | Amount of Sieve Added grams | Final $H_2O$ Content % | AZAD g/l | Capacity g $H_2O$/g mole sieve |
|---|---|---|---|---|
| A | 0 | 16.5 | 4.5 | — |
| B | 20 | 12.6 | 4.8 | 0.19 |
| C | 30 | 10.8 | 4.9 | 0.21 |
| D | 40 | 8.1 | 4.7 | 0.20 |
| E | 80 | 1.1 | 5.1 | 0.193 |

EXAMPLE 2

Samples from Example 1 were then formulated into a usable formulation by blending in Tween-20, neem oil, PABA, and punctilious ethanol. The final content of each formulation was made-up to contain 20% Tween-20, 10% neem oil, 1% PABA, and pH 3.8. The samples were then placed in sealed containers, stored at 55° C in an incubator, and periodically assayed for Azadirachtin A content.

TABLE II

| Azadirachtin A Content of Formulated Samples | | | | | | | |
|---|---|---|---|---|---|---|---|
| | | Hours of Storage at 55° C. | | | | | |
| Sample | % $H_2O$ | 0 | 100 | 268 | 480 | 1008 | 1280 |
| A | 11.0 | 2.9 | 2.3 | 1.6 | 0.99 | .3 | .21 |
| D | 6.0 | 2.9 | 2.6 | 2.0 | 1.4 | .62 | .47 |
| E | 0.8 | 2.8 | 2.7 | 2.5 | 2.1 | 1.3 | 1.0 |

Results show Conclusively that low water content formulation is more stable.

EXAMPLE 3

Multi-Stage Extraction of Azadirachtin with Methylethylketone (MEK)

The extraction procedure was carried out in a batch operation by grinding two kilograms of neem seeds to a five-mesh particle size, extracting the neem oil from the ground seeds by placing them in a 15 liter glass vessel with ten liters of hexane and agitating for 24 hours at room temperature. The solvent was filtered through #41 Whatman paper and the dry seed cake was retained. The defatted seeds were divided into five lots weighing 500 grams each.

The multi-stage extraction of azadirachtin with MEK was run at 60° C. for five hours under atmospheric pressure. The first lot of seeds was placed in a two liter, single neck, round bottom flask to which one liter of MEK was added. The flask was connected to a Rotovap and operated at the stated conditions. Solvent recovery was by filtration through a Buchner funnel using #41 Whatman paper. The recovered solvent was stored overnight at room temperature in a one liter polyethylene bottle. The solvent volume was adjusted to one liter using fresh MEK prior to each successive extraction.

The MEK extract was formulated by adding 20% Tween 20 and 1% PABA, blended and placed in an oven at 55° C. and sampled periodically for the preserve of Azadirachtin A. The results presented in Table III show that the MEK extract had much greater shelf-stability than the ethanol extract with 11% $H_2O$.

TABLE III

| Time at 55° C. (hours) | Azadirachtin (g/l) | |
|---|---|---|
| | MEK | 11% $H_2O$/Ethanol |
| 0 | 3.1 | 2.9 |
| 100 | 2.9 | 2.3 |
| 216 | 3.1 | 1.6 |
| 480 | 2.7 | .99 |

EXAMPLE 4

A crude ethanol extract of neem seed containing both Azadirachtin A and Azadirachtin B was diluted with an aprotic solvent to provide the desired solvent mixture. In several cases (lines 5 and 6), water was added to increase the water content of the mixture. The 100% propyl acetate solution (line 7) was prepared by dissolving a mixture of solid Azadirachtin A and Azadirachtin B (isolated using the process described by D. R. Schroeder and K. Nakanishi, *J. Natural Products*, 50, 241-284 (1987)) in reagent grade propyl acetate (PrOAc) that had been dried over 3 Angstrom molecular sieves. For each solvent system, the original solution was split. One portion was used to determine the initial water content and initial azadirachtin concentrations. The remaining portion was placed in a sealed vial and heated at 75° C. for the time indicated. The heated samples were then analyzed for azadirachtin content. Table IV indicates the relative amount of azadirachtin that remained after heating.

TABLE IV

Effect of Aprotic Solvent of Azadirachtin Stability

| | % Aprotic | Aprotic | % $H_2O$ | AZAD A** | AZAD B** |
|---|---|---|---|---|---|
| 1 | — | — | 7.6 | 51 | 77 |
| 2 | 25 | PrOAc | 5.7 | 66 | 95 |
| 3 | 50 | PrOAc | 3.8 | 75 | 100 |
| 4 | 75 | PrOAc | 1.9 | 84 | 96 |
| 5 | 75 | PrOAc | 6.2 | 80 | 92 |
| 6 | 75 | PrOAc | 10.5 | 80 | 95 |
| 7 | 100 | PrOAc | — | 116 | 113 |
| 8 | 25 | 2-butanone | 5.7 | 78 | 95 |
| 9 | 50 | 2-butanone | 3.8 | 71 | 88 |
| 10 | 75 | 2-butanone | 1.9 | 83 | 90 |
| 11 | — | 2-butanone | — | 47* | 17* |
| 12 | — | Tween 20 | — | 76* | 103* |
| 13 | 20/10 | Tween 10/ Neem Oil | — | 80* | 105* |
| 14 | 25/15 | Tween 20/ Neem Oil | 4.0 | 50* | 84* |

**% of original concentration after 40 hours at 75° C.
*after 48 hours at 75° C.

EXAMPLE 5

A crude mixture, containing 8% Azadirachtin A and 6% Azadirachtin B, obtained from a purified neem seed extract (prepared according to the process described by D. R. Schroeder and K. Nakanishi, *J. Natural Products*. 50, 241-284 (1987)) was dissolved in each of the solvents indicated in Table V. The reagent grade solvents were dried over 3 Angstrom 5 molecular sieves prior to use. For each solvent or solvent combination, the initial solution was split into three portions. One of the three was used to determine the water content and initial azadirachtin concentrations. The remaining samples were placed in sealed vials and heated at 75°-85° C. for 48 hours. The samples were then analyzed for azadirachtin content. Table V indicates the relative amount of azadirachtin that remained after heating.

TABLE V

Stability of Azadirachtin in Different Solvents

| | w/w | Azadirachtin** | |
|---|---|---|---|
| Solvent | % $H_2O$ | AZAD A | AZAD B |
| 1) Methanol | 0.18 | 80 | 97 |
| 2) Ethanol | 0.23 | 67 | 90 |
| 3) n-Propanol | 0.10 | 78 | 92 |
| 4) n-Butanol | 0.09 | 78 | 91 |
| 5) t-Butanol | 0.07 | 86 | 94 |
| 6) Acetone | 0.06 | 99 | 100 |
| 7) Acetonitrile | 0.31 | 92 | 93 |
| 8) 2-Butanone/Ethanol* | 2.1 | 90 | 100 |
| 9) 2-Butanone/Ethanol* | 4.0 | 90 | 97 |
| 10) 2/Butanone/Ethanol* | 11.8 | 78 | 93 |
| 11) Dimethyl Sulfoxide | 0.10 | 72 | 72 |
| 12) Dimethyl Formamide | 0.12 | 78 | 76 |
| 13) Dimethyl Acetamide | 0.16 | 110 | 112 |

*3:1 ratio of 2-Butanone/Ethanol.
**% Azadirachtin remaining after 48 hours at 75-83° C.

What is claimed is:

1. A storage-stable pesticide composition comprising a neem seed extract solution containing azadirachtin wherein the solution has at least 50% by volume aprotic solvent, at least about 1.0% but less than 10% surfactant, and less than 15% by volume water, said solution being non-degrading to azadirachtin.

2. A storage-stable pesticide composition according to claim 1 wherein the aprotic solvent is selected from the group consisting of nitriles, substituted aromatics, chlorinated aliphatics, aromatic aldehydes, sulfones, ethers, esters, amides, sulfoxides, alkyl carbonates, ketones, and mixtures thereof.

3. A storage stable pesticide composition according to claim 1 wherein the solution further includes 0 to 40% neem oil, 0 to 1 percent para-aminobenzoic acid or its esters, and the pH is adjusted to between 3.8 and 4.2 with the addition of sodium hydroxide or acetic acid, wherein the percentages are on a weight/weight basis.

4. A storage-stable pesticide composition comprising neem seed extract solution containing azadirachtin wherein the solution has at least 50% by volume alcohol solvent, at least about 1.0% but less than 10% surfactant, and less than 5% by volume water, said solution being non-degrading to azadirachtin.

5. A storage-stable pesticide composition according to claim 4 wherein the solution has at least 50% by volume alcohol solvent and less than 2% by volume water.

6. A storage-stable pesticide composition according to claim 4 wherein the solution has at least 50% by volume alcohol solvent and less than 1% by volume water.

7. A storage stable pesticide composition according to claim 4 wherein the alcohol solvent is selected from the group consisting of methanol, ethanol, propanol, isopropanol, butanol, 2-butanol, t-butanol, benzyl alcohol and mixtures thereof.

8. A storage stable pesticide composition according to claim 4 the solution further includes 0 to 40% neem oil, 0 to 1 percent para-aminobenzoic acid or its esters, and the pH is adjusted to between 3.8 and 4.2 with the addition of sodium hydroxide or acetic acid, wherein the percentages are on a weight/weight basis.

9. A process for the preparation of a storage-stable pesticide composition comprising the steps of:
  a. extracting neem oil from coarsely ground neem seeds with a non-polar azadirachtin-insoluble aprotic solvent,
  b. extracting azadirachtin from the defatted neem seeds with a polar aprotic solvent, and
  c. adjusting the azadirachtin extract from (b) by diluting with additional aprotic solvents or further extracting with a water-immiscible aprotic solvent to obtain a storage-stable pesticide composition having greater than 50% by volume aprotic solvent, at least about 1.0% but less than 10% surfactant, and less than 15% by volume water.

10. A process according to claim 9 wherein the aprotic solvent is selected from the group consisting of ketones, nitriles, substituted aromatics, chlorinated aliphatics, aromatic aldehydes, sulfones, ethers, esters, amides, sulfoxides, alkyl carbonates, and mixtures thereof.

11. A process for the preparation of a storage-stable pesticide composition comprising the steps of:
  a. extracting neem oil from coarsely ground neem seeds with a non-polar azadirachtin-insoluble aprotic solvent,
  b. extracting azadirachtin from the defatted neem seeds with a alcohol solvent, and
  c. adjusting the azadirachtin extract from (b) by either diluting or further extracting with a water-immiscible aprotic solvent to obtain a storage-stable pesticide composition having greater than 50% by volume alcohol solvent, at least about 1.0% but less than 10% surfactant, and less than 5% by volume water.

12. A process according to claim 11 wherein the composition has at least 50% by volume alcohol solvent and less than 2% by volume water.

13. A process according to claim 11 wherein the composition has at least 50% by volume alcohol solvent and less than 1% by volume water.

14. A process according to claim 11 wherein the alcohol solvent is selected from the group consisting of methanol, ethanol, propanol, isopropanol, butanol, 2-butanol, t-butanol, benzyl alcohol, and mixtures thereof.

15. A process for the preparation of a storage-stable pesticide composition comprising the steps of:
  a. extracting azadirachtin and neem oil from coarsely ground neem seeds with a polar aprotic solvent, and
  b. adjusting the azadirachtin extract from (a) by either diluting or further extracting with a water-immiscible aprotic solvent to obtain a storage-stable pesticide composition has greater than 50% by volume aprotic solvent, at least about 1.0% but less than 10% surfactant, and less than 15% by volume water.

16. A process according to claim 15 wherein the polar aprotic solvent is selected from the group consisting of ketones, nitriles, substituted aromatics, chlorinated aliphatics, aromatic aldehydes, sulfones, ethers, esters, amides, sulfoxides, alkyl carbonates, and mixtures thereof.

17. A process for the preparation of a storage-stable pesticide composition comprising the steps of:
  a. extracting azadirachtin and neem oil from coarsely ground neem seeds with an alcohol solvent, and
  b. adjusting the azadirachtin extract from (a) by either diluting or further extracting with a water-immiscible aprotic solvent to obtain a storage-stable pesticide composition having greater than 50% by volume alcohol solvent, at least about 1.0% but less than 10% surfactant, and less than 5% by volume water.

18. A process according to claim 17 wherein the composition has at least 50% by volume alcohol solvent and less than 2% by volume water.

19. A process according to claim 17 wherein the composition has at least 50% by volume alcohol solvent and less than 1% by volume water.

* * * * *

REEXAMINATION CERTIFICATE (3647th)

United States Patent [19]

Carter et al.

[11] B1 5,124,349

[45] Certificate Issued Oct. 20, 1998

[54] STORAGE STABLE AZADIRACHTIN FORMULATION

[75] Inventors: Charles G. Carter, Silver Spring; Clifford J. Hull, Jr., Laurel; Narender P. Luthra, Columbia; James F. Walter, Ashton, all of Md.

[73] Assignee: W. R. Grace & Co.-Conn., New York, N.Y.

Reexamination Request:
No. 90/004,050, Dec. 8, 1995

Reexamination Certificate for:
Patent No.: 5,124,349
Issued: Jun. 23, 1992
Appl. No.: 606,366
Filed: Oct. 31, 1990

Related U.S. Application Data

[63] Continuation-in-part of Ser. No. 371,243, Jun. 26, 1989, Pat. No. 5,001,146.

[51] Int. Cl.$^6$ .................................................. A01N 43/16
[52] U.S. Cl. ........................................ 514/453; 424/195.1
[58] Field of Search ........................... 424/195.1; 514/453

[56] References Cited

U.S. PATENT DOCUMENTS

| | | | |
|---|---|---|---|
| 4,556,562 | 12/1985 | Larson | 424/195.1 |
| 5,124,349 | 6/1992 | Sakata et al. | |

OTHER PUBLICATIONS

Feverhake "Effectiveness & Selectivity of Technical Solvents for the Extraction of Neem Seed Components with Insecticidal Activity" Process 2nd Int. Neem Conf. Ravischholzhausen, 1983. pp. 103–114.

Letter from Dr. George Kabalka, University of Tennessee, Knoxville, Department of Chemistry, Robert H. Cole Professor, Nov. 3, 1995.

International Patent Application No. PCT/AU90/00487, "Head Lice Treatment", Oct. 10, 1989 (and accompanying letter from inventor).

Letter for Dr. Madeline Adamczeski, American University Department of Chemistry, Oct. 11, 1995.

Letter of Dr. Thomas H. Brownlee, American University, Department of Chemistry, Visiting Professor, Oct. 27, 1995.

Letter from M.N. Sukhatme, Research Director Herringer Bright Chemicals to United States Patent and Trademark Office (Sep. 19, 1995).

Letter from R.P. Singh, Senior Scientist of the Indian Agricultural Research Institute, to Dr. Vandana Shiva, Director of the Science Technology and Natural Resource Policy (Jun. 22, 1993).

Letter from B.N. Dhawan of the Central Drug Research Institute, to Dr. Vandana Shiva, Director of Science Technology and Natural Resource Policy (Jun. 14, 1993).

S.S. Gupta and C.R. Mitra, "The Component Acids and Glycerides of Refined Neem (Melia Indica) Oil", *J. Sci. Food Agric.*, vol. 382, Jan. 4, 1953, at 44.

D. Schroeder and K. Nakanishi, "A Simplified Isolation Procedure for Azadirachtin", *Journal of Natural Products*, vol. 50, 1987, at 241.

R. Yamasake, et al., "Isolation and Purification of Azadirachtin from Neem Seeds Using Flash Chromatography and High Performance Liquid Chromatography", *Journal of Chromatography*, vol. 356, 1986, at 220.

P. Chandra and J.G. Shrikhande, "Effect of Fat on Mineralization of Nitrogen in Some Oil–Cakes and Wool–Waste", *Agra University Journal of Research*, vol. IV, Part I, Jan. 1955, at 25.

Dr. Vandana Shiva and Radha Holla–Bhar, "Intellectual Piracy and the Neem Tree", *The Ecologist*, No. 6, Nov./Dec. 1993.

Richard Stone, "A Biopesticidal Tree Begins to Blossom", *Science*, vol. 255, Feb. 28, 1992, at 1070–1071.

Saleem Ahmed and Michael Grainge, "Potential of the Neem Tree (Azadirachta indica) for Pest Control and Rural Development", *Economic Botany*, vol. 40(2), 1986, at 201–207.

Dr. S. Radwanski, "Neem Tree—Commercial Potential, Characteristics and Distribution", *World Crops and Livestock*, Mar./Apr. 1977, at 63–66.

National Research Council Report, *Neem, a Tree for Solving Global Problems*, National Academy Press, Washington, D.C., 1992, at 5–32.

M.G. Jotwani and K.P. Srivastava, "A Review of Neem Research in India in Relation to Insects", *Schriftenr–Ges–Tech–Zusammenarbeit: Die Gesellschaft*, vol. 161, 1984, at 35–53.

Fred Pierce, "Pesticide Patent Angers Indian Farmers", *New Scientist*, Oct. 9, 1993, at 7.

"Farmers Burn Dunkel Effigy at Lal Quila Rally," *The Telegraph*, May 1995.

K. Feuerhake and H. Schmutterer, "Development of a Standardized and Formulated Insecticide From a Neem Kernal Extract", *Journal of Plant Diseases and Protection*, vol. 92(6), 1985, at 643.

Bruce Rensberger, "Is Any Tree As Useful As a Neem", *Washington Post*, Feb. 17, 1992, at A3.

Gary Stix, "Village Pharmacy", *Scientific American*, May 1992, at 132.

Hiram G. Larew, "The Neem Tree", *American Horticulturist*, Aug. 26, 1988, at 25–27.

"Pesticide Tea", *Discover*, Jul. 1992, at 14.

(List continued on next page.)

*Primary Examiner*—Herbert J. Lilling

[57] ABSTRACT

Storage stable pesticide compositions comprising neem seed extracts which contain azadirachtin as the active pesticidal ingredient wherein the compositions are characterized by their non-degrading solvent systems. In a first embodiment, the pesticide compositions contain solvent systems characterized as having greater than 50% by volume aprotic solvents and less than 15% by volume water. In a second embodiment, the pesticide compositions contain solvent systems characterized as having greater than 50% by volume alcohol and less than 5% by volume water. The pesticide compositions contain surfactant concentrations of at least about 1.0%, up to 10%.

OTHER PUBLICATIONS

S.K. Gosh, G.D. Verma and B.S. Lall, "Pesticidal Efficacy of Some Indigenous Plant Products Against Pulse Beetle Callosobruchus (Pachymerus) Chinesis Linn", *Bulletin of Grain Technology*, vol. 19(2), Aug. 1981, at 96–98.

C.R. Narayanan, R.P. Singh and D.D. Sawaikar, "Phagodeterrency of Various Fractions of Neem Oil Against Schistocerca Gregaria F.", *Pesticides*, Nov. 1978, at 32.

Walter Lewis and P.F. Elvin Lewis, "Neem Cultivated in Haiti", *Economic Botany*, vol. 37(1), 1983, at 70.

T.L. Ladd, M. Jacobson and C.R. Buriff, "Japanese Beetles: Extracts from Neem Tree Seeds as Feeding Deterrents", *Journal of Economic Entomology*, vol. 71(5), Oct. 1978, at 810.

B.G. Joshi and S. Sitaramaiah, "Neem Kernel as an Ovipositional Repellant for Spodoptera Litura (F.) Moths", *Phytoparasitica*, vol. 7(3), Nov. 1979, at 199.

J. Meisner, M. Kehat, M. Zur and C. Eizick, "Response of Earias Insulana Boisd Larvae to Neem Kernal Extract", *Phytoparasitica*, vol. 6(2), 1978, at 85.

P. Savitri and C.S. Rao, "Studies on the Admixture of Neem Seed Kernal Powder With Paddy in the Control of Important Storage Pests of Paddy", *Andhra Agricultural Journal*, vol. 23 (3 & 4), May/Aug. 1977, at 137–143.

B.G. Joshi, G. Ramaprasad and S.V. Satyanarayana, "Relative Efficacy of Neem Kernel, Fentin Acetate and Fentin Hydroxide as Antifeedants Against Tobacco Caterpillar, Spodoptera Litura Fabricius, in the Nursery", *Indian Journal of Agricultural Science*, vol. 48(1), Jan. 1978, vol. 48(1), at 19–22.

G.K. Girish and S.K. Jain, "Studies on the Efficacy of Neem Seed Kernal Powder Against Stored Grain Pests", *Bulletin of Grain Technology*, Dec. 1974, vol. 12(3), at 226–228.

B.G. Joshi and G. Ramaprasad, "Neem Kernel as an Antifeedant Against the Tobacco Caterpillar", *Phytoparasitica*, vol. 3(1), Jun. 1975, at 59–61.

A. Abdul Kareem, S. Sadakathulla, M.S. Venugopal and T.R. Subramaniam, "Efficacy of Two Organotin Compounds and Neem Extract Against the Sorghum Shoot Fly", *Phytoparasitica*, vol. 2(2), Dec. 1974, at 127.

Dr. S. Radwanski, "Neem Tree: Further Uses and Potential Uses", *World Crops and Livestock*, vol 29 (4), Jul./Aug. 1977, at 167–168.

G. Jiliani and M.M. Malik, "Studies on Neem Plant as Repellant Against Stored Grain Insects", *Pakistan Journal of Science and Indian Research*, Dec. 1973, vol. 16(6), at 251–254.

J. H. Butterworth and E.D. Morgan, "Investigation of the Locust Feeding Inhibition of the Seeds of the Neem Tree, Azadirachta Indica", *Journal of Insect Physiology*, vol. 17(6), Jun. 1971, at 969–977.

R.G. Pierce, "Neem Tree Seed Extracts Repel Japanese Beetles Popillia Japonica", *USDA Agricultural Research*, vol. 27(9), Mar. 1979, at 8–10.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 are confirmed.

* * * * *